United States Patent [19]

Hwang et al.

[11] Patent Number: 4,912,528

[45] Date of Patent: Mar. 27, 1990

[54] TRACE METALS ANALYSIS IN SEMICONDUCTOR MATERIAL

[75] Inventors: Lydia L. Hwang; James R. McCormick, both of Midland, Mich.

[73] Assignee: Hemlock Semiconductor Corporation, Hemlock, Mich.

[21] Appl. No.: 214,352

[22] Filed: Jul. 1, 1988

[51] Int. Cl.[4] .............................................. G01N 1/00
[52] U.S. Cl. ...................................... 356/36; 356/311
[58] Field of Search ...................................... 356/36, 311

[56] References Cited

U.S. PATENT DOCUMENTS 3,954,336  5/1976  Baird et al. ............................ 356/36
4,338,029  7/1982  Macourt ................................ 356/311

OTHER PUBLICATIONS

Dietze et al., "Float–Zone Grown Silicon"; Crystal Growth Properties and Applications, vol. 5, 1981.
Associated Industries Ltd. Publication 2030/A16, Oct. 1960.
Martin, *Semiconductor Silicon*, ed. by R. R. Haberecht, p. 547 (1969).
Heinen et al., Anal. Chem., 38(13), p. 1853 (1966).
Thompson et al., *Anal. Chem.*, 30(6), p. 1023 (1958).
Stewart et al., *Analyst*, 108, p. 1450 (1983).
Taddia, *Anal. Chim. Acta.*, 142, p. 333 (1982).
Fuller, Anal. Chim. Acta., 62, p. 261 (1972).
Dietz et al., *Cryst.: Growth, Prop, Appl.*, 5 (1981), pp. 1–42.
Mollenkopf et al., DOE/JPL–954331–80/9, (Jan., 1980), pp. 54–55.
Kirk–Othmer, Encyclopedia of Chemical Technology, 2nd Ed., vol. 17, pp. 862–865.

*Primary Examiner*—Léon Scott, Jr.
*Attorney, Agent, or Firm*—Carl A. Yorimoto; James E. Bittell

[57] ABSTRACT

A method for analyzing and quantifying the individual trace metals content of a semiconductor material in the low to sub-parts per billion (ppba) range. The method comprises (A) float-zone refining of a sample of the semiconductor material creating a melt zone containing essentially all the trace metals of the sample; (B) cooling the melt zone to form a solid zone concentrated in trace metals; (C) separating the solid zone concentrated in trace metals from the sample of the semiconductor material; (D) converting the solid zone concentrated in trace metals into a form suitable for trace metals analysis; (E) analyzing the solid zone with known trace metals analytical techniques; and (F) calculating total trace metals from these analytical results. This method can also be applied to the small tip which forms on the side of the solid zone.

10 Claims, 1 Drawing Sheet

TRACE METALS ANALYSIS IN SEMICONDUCTOR MATERIAL

BACKGROUND OF THE INVENTION

This invention relates to the analysis of trace metal impurities in semiconductor materials. More specifically this invention relates to an improved technique for determining the content of these trace metals in the low to sub-part per billion, atomic, (ppba) range.

Because of the extremely high performance demands of the electronics industry, semiconductor materials of extremely high purity are required. Analytrical techniques to characterize extremely low levels (ppba) of trace metals are becoming a necessity. The development of appropriate analytical techniques has been on-going for many years. As an example, trace metal analysis in semiconductor silicon at low (ppba) levels has been attempted with many analytical techniques. Examples of such techniques are mass spectrometry, neutron activation analysis, and atomic absorption spectrometry.

Spark source mass spectrometry, as noted in Associated Electrical Industries Ltd. Publication 2030/A16, Oct.,1960, has been utilized to analyze such metals as chromium, copper, iron, and nickel to levels down to about 100, 50, 300, and 500 ppba, respectively. This technique only measures point samples and not bulk samples. This technique involves a very small area of a sample surface which may not be representative of the bulk of the sample.

One of the more sensitive analytical techniques is neutron activation analysis. This technique is described in several references, including: Martin, Semiconductor Silicon, Ed. by R. R. Haberecht, p. 547 (1969); Heinen et al., Anal. Chem., 38 (13), p. 1853 (1966); and Thompson et al., Anal. Chem., 30(6), p. 1023 (1958). While this technique is quite sensitive, a large neutron-generating radiation source is necessary. Additionally, several weeks can be required to complete the monitoring of the radioactive decay of the nucleides generated. Thus, this technique is both expensive and time-consuming.

Atomic absorption spectrometry for the analysis of trace metals in silicon has been improved by going from a flame technique tp flameless graphite furnace technique. Sensitivity in the picogram range is now possible. This flameless graphite furnace technique has been used by many investigators in the following references: Stewart et al., Analyst, 108, p. 1450 (1983); Taddia, Anal. Chim. Acta, 142, p. 333 (1982); and Fuller, Anal. Chim. Acta, 62, p. 261 (1972). This technique requires that a sample be placed in solution before analysis. More significantly, because of the low levels of metal for which detection is being attempted, very meticulous, time-consuming procedures must be applied to prevent background contamination from masking the analysis being attempted.

In all of the above techniques contamination in sample preparation can mask results when semiconductor samples of low trace metal content are analyzed.

SUMMARY OF THE INVENTION

The objective of the instant invention is to provide a reliable analytical technique that is time and cost effective and can be used as a routine trace metals contaminant analysis.

It has been found that the float-zone refining technique will concentrate most trace metal impurities significantly. As an example, with semiconductor silicon this concentration factor can be large, ranging from 20 to over 200 times the level in the bulk semiconductor silicon sample. Such a sample concentrated with essentially all the trace metal impurities of the bulk sample can be processed by many known trace metal analytical techniques to reliably define levels of the trace metal impurities that are present in the bulk sample in the ppba or sub-ppba range.

DESCRIPTION OF THE DRAWING

FIG. 1 is presented for the purposes of illustration and is not to be construed as limiting the instant invention as claimed herein.

In FIG. 1, a seed crystal rod 1, essentially free of impurities, is fused to a rod 7 of semiconductor material to be refined to begin the float-zone refining procedure. As the annular heater of the float-zone refining apparatus passes from the juncture 2 of the seed crystal 1 and the rod 7, a molten zone 3 moves up the rod, leaving behind a solid single crystal 4 of semiconductor material essentially free of trace metals, the trace metals being concentrated in the molten zone 3. As the end of the rod 7 is reached, the molten zone 3 is allowed to cool to a solid zone 5. Cooling of the molten zone 3 is controlled so that a frozen tip 6 of a desired size forms on the side of the solid zone 5. The combined solid zone 5 and tip 6 contain essentially all the trace metals that were present in the starting rod of semiconductor material to be refined.

DESCRIPTION OF THE INVENTION

Figure 1:
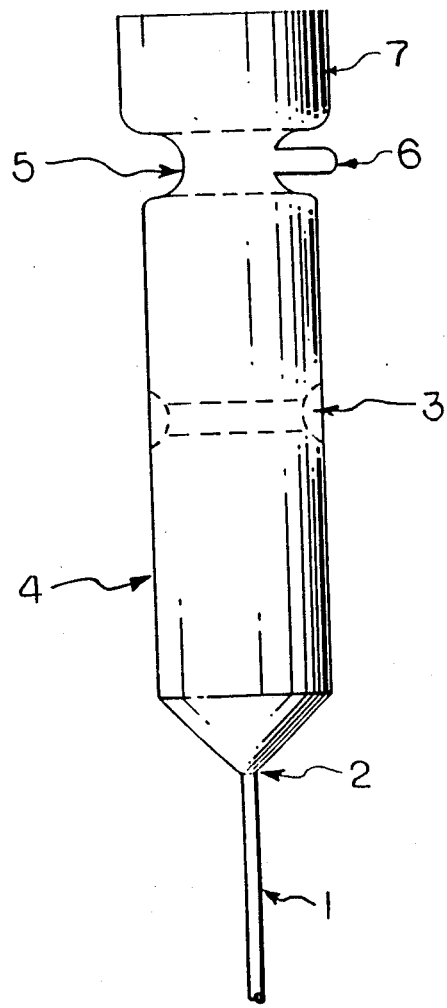
FIG. 1 is a representation of a rod of a semiconductor material that has been subjected to a float-zone refining process.

In accordance with the instant invention there is provided a method for the analysis of and determination of the level of trace metals in a semiconductor material under conditions that will be delineated herein. What is desired, therefore, is a method for analyzing and quantifying the individual trace metals content of a semiconductor material, said semiconductor material being suitable for float-zone refining, said method comprising (A) performing float-zone refining of a sample of the semiconducotr material, creating a melt zone containing essentially all the trace metals;

(B) cooling the melt zone to form a solid zone concentrated in trace metals, said solid zone containing essentially all the trace metals of the sample of the semiconductor material;

(C) separating the solid zone concentrated in trace metals from the sample of the semiconductor material;

(D) converting the solid zone concentrated in trace metals into an aqueous solution suitable for trace metals analysis;

(E) analyzing the aqueous solution from (D) with a means for trace metals analysis; and (F) calculating total trace metals content of the sample of the semiconductor material analysis of the aqueous solution from (E).

The semiconductor material can be, for example, silicon, germanium, or gallium arsenide. Silicon is the semiconductor material of greatest interest.

The trace metal impurities for which this method analyzes and quantifies can be, for example, aluminum, chromium, copper, iron, manganese, molybdenum, nickel, and titanium.

The float-zone refining technique to purify semiconductor materials is a known method in the art. Float-zone refining can be carried out in a manner described by Dietz et al., *Cryst.: Growth, Prop., Appl.*, 5 (1981), pp. 1–42. The float-zone technique creates a zone of molten material that moves along the sample of the semiconductor material as a heating element of the device passes leaving a rod of single crystal semiconductor material. The trace metals are concentrated in this molten zone because of the greater solubility of these trace metals in the melt compared to trace metals solubility in the solid. The relationship of the concentration of the trace metals in the melt and solid are defined by the segregation coefficient of these metals in the semiconductor material. As an example of such segregation coefficients, the segregation coefficient, $K_{eff}$, for certain metals in silicon has been determined by Mollenkopf and McCormick, DOE/JPL-954331-80/9, (Jan., 1980), pp. 54–55. The segregation coefficient for several metals are listed in the following table:

| Metal | $K_{eff}$ |
| --- | --- |
| Tungsten | $1.7 \times 10^{-8}$ |
| Molybdenum | $4.5 \times 10^{-8}$ |
| Iron | $6.4 \times 10^{-6}$ |
| Chromium | $1.1 \times 10^{-5}$ |
| Manganese | $1.3 \times 10^{-5}$ |
| Nickel | $1.3 \times 10^{-4}$ |
| Copper | $8.0 \times 10^{-4}$ |

Thus, float-zone refining concentrates trace metals as much as several orders of magnitude. The preparation of a sample only a fraction of the size of the bulk sample with impurities at a concentrated level allows greater sensitivity in analyzing for trace metals which exist in the bulk sample at low to sub-part per billion levels.

The size of the frozen melt zone relative to the total sample of the semiconductor material varies with such factors as the size of the single crystal to be formed, and the melting and cooling conditions. The frozen melt zone can be in a range from about 0.1 to 5 weight percent of the total sample of the semiconductor material.

In cooling the melt zone, because of the differences in the specific gravities of the solid and molten semiconductor material, a bulge or "freeze-out tip" may form at the side of the frozen melt zone. This frozen tip is only a fraction of the weight of the total frozen melt zone. The formation of the tip relative to the frozen melt zone is illustrated in FIG. 1, supra. The size of the tip relative to the size of the frozen melt zone varies with the size of the melt zone and the cooling conditions as the melt zone is freezing. The frozen tip can be in the range from about 1 to 10 weight percent of the frozen melt zone. Additionally, the tip, being the last portion of the molten zone to solidify is more greatly concentrated in the trace metals than the bulk of the frozen zone. As an example, for a rod of semiconductor silicon, the tip can contain about 25 to 40 percent of the total trace metals. Thus, the method described above an also be applied only to the frozen tip of the frozen melt zone. As such, what is described is a method for analyzing for and quantifying the individual trace metals content of a semiconductor material, said semiconductor material being suitable for float-zone refining, said method comprising (G) performing float-zone refining of a sample of the semiconductor material, creating a melt zone containing essentially all the trace metals;

(H) controlling cooling of the melt zone so that the melt zone forms a solid zone with a frozen tip being formed, said frozen tip containing a significant portion of the trace metals of the sample of the semiconductor material;

(J) separating the frozen tip from the solid zone;

(K) preparing thre frozen tip for trace metals analysis;

(L) analyzing the frozen tip with a means for trace metals analysis; and (M) calculating total trace metals content of the sample of the semiconductor material from analysis of the frozen tip.

The physical form of the sample of semiconductor material is not critical so long as it is suitable for the float-zone refining techniques. An example of a suitable form is a rod. The sample can be either polycrystalline material or single crystal material. The polycrystalline material can be produced by a known technique such as the chemical vapor decomposition of a precursor of the semiconductor material and subsequent deposition of the semiconductor material. The single crystal rod may be formed by pulling a crystal from a molten mass of the semiconductor material via a known technique such as the Czochralski crystal pulling method or the float-zone refining method.

For the determination of trace metals concentration from analysis of a sample of the frozen tip formed on the frozen melt zone, cooling conditions are established to form, relatively reproducibly, a frozen tip of similar size and similar proportion of the trace metals of the total frozen melt zone. A preferred cooling procedure to assure the formation of an adquately sized frozen tip is (a) reducing electrical power to the heating coil of the zone refiner over a period of from about 5 to 10 seconds; (b) carefully removing the coil from around the rod so that the tip does not touch the hot coil; and (c) cooling to ambient temperature.

Separating the solidified melt zone from the rod of semiconductor material can be effected by known means such as, for example, cutting with a diamond tipped saw. Further, separating the frozen tip from the solidified melt zone can also be effected by known means such as, for example, scribing with a diamond stylus.

The total frozen melt zone or the frozen tip from the frozen melt zone can be analyzed dissolved in an aqueous sample or as a solid sample. Analysis of the frozen melt zone or the frozen tip as a dissolved aqueous sample is the preferred route, since the trace metals will be more homogenously dispersed in the liquid sample. In analysis of the total frozen melt zone or the frozen tip as a solid by such techniques as emission spectroscopy or X-ray diffraction, the result is a point analysis. For accuracy, a solid sample should be analyzed in different positions relative to the analytical means, the results being averaged.

Means for trace metals analysis can be such known techniques, as for example, atomic absorption spectroscopy, for example, graphite furnace atomic absorption spectroscopy; electron spectroscopy, for example, auger electron spectroscopy; emission spectroscopy. for example, inductively coupled plasma atomic emission spectroscopy; ion chromatography; mass spectrometry; deep level transient spectroscopy; and X-ray spectroscopy, for example, energy dispersive X-ray spectroscopy. Graphite furnace atomic absorption spectroscopy is a preferred means for trace metals analysis.

Many analytical techniques, such as graphite furnace atomic absorption spectroscopy, for example, require a liquid sample. Thus, the solid semiconductor material to be analyzed must be placed into solution. Known reagents such as, for example, strong mineral acids and the like can be utilized. Additionally, the solid sample can be treated before dissolution to remove surface contamination due to handling of the sample. As an example of such a procedure, for preparing a sample of silicon the following procedure can be used for either the frozen melt zone or the frozen tip:

(a) treating the solid sample with electronic-grade solvent to remove surface contamination;
(b) etching the solid sample with an acid mixture, comprising electronic-grade nitric acid and electronic-grade hydrofluoric acid to further remove surface contamination;
(c) rinsing the etched solid sample in deionized water;
(d) dissolving the solid sample in an acid mixture, comprising doubly distilled nitric acid and hydrofluoric acid;
(e) drying the acid mixture from (d) to a solid residue;
(f) dissolving the solid residue in an acid mixture, comprising doubly distilled nitric acid and hydrofluoric acid;
(g) diluting the mixture of dissolved solid concentrate and nitric and hydrofluoric acid with distilled water.

Preparation of a solid sample for analysis can follow, as an example, a procedure outlined by steps (a) through (c) above.

Once a suitable liquid sample has been prepared, a portion of the sample is injected into the means for trace metals analysis. Once a suitable solid sample has been prepared, the solid sample is appropriately positioned in the analytical apparatus.

The trace metals content of the total sample of the semiconductor material is calculated from the analysis of an aqueous sample or the solid frozen tip of the melt zone. As an example of such calculations, the results of the graphite furnace atomic absorption spectroscopy (GFAA), which are reported in nanograms of metal per milliliter of solution (ng/ml), will be used. For the determination of trace metals concentration from GFAA analysis of a sample of the total frozen melt zone, trace metals content is calculated from GFAA results using the following relationship:

$C_t = [C_{fmz} - C_b] \times V_{fmz} / W_t$, wherein, $C_t$ = the concentration of the metal in the total silicon sample, ng/g
$C_{fmz}$ = GFAA analysis of sample solution prepared from the frozen melt zone, ng/ml
$C_b$ = GFAA analysis of blank solution, ng/ml
$V_{fmz}$ = volume of the sample solution prepared from the frozen melt zone, ml
$W_t$ = weight of the total silicon sample, g The calculated results are converted from ppbw to ppba.

Once the relationship of the proportions of trace metals in the frozen tip to the total frozen melt zone is established, trace metals content is calculated from GFAA results using the following relationship:

$C_t = 1/F \times [C_{ft} - C_b] \times V_{ft}/W_t$, wherein, $C_t$ = the concentration of the metal in the total silicon sample, ng/g
$F$ = fraction of total trace metals, relative to the total frozen melt zone, contained in the frozen tip
$C_{ft}$ = GFAA analysis of sample solution prepared from the frozen tip, ng/ml
$C_b$ = GFAA analysis of blank solution, ng/ml
$V_{ft}$ = volume of the sample solution prepared from the frozen tip, ml
$W_t$ = weight of the total silicon sample, g The calculated results are converted from ppbw to ppba.

So that those skilled in the art may better understand and appreciate the instant invention, the following examples are presented. These examples are presented to be illustrative and are not to be construed as limiting the claims of the instant invention.

EXAMPLE 1: (not within the scope of the instant invention)

Samples of silicon, essentially free of metals, and an acid solution similar to that in which the final sample is prepared were analyzed by graphite furnace atomic absorption spectroscopy (GFAA) to determine the detection limits of this analytical technique.

The sample of silicon, essentially free of metals, was prepared by a zone-refining technique similar to that which will be described in subsequent examples.

The following procedure was utilized to prepare samples suitable for GFAA. A 0.1 g sample of the silicon, essentially free of metals, was placed in an acid mixture consisting of 1 ml concentrated nitric acid and 2 ml concentrated hydrofluoric acid. This mixture was allowed to heat overnight and to evaporate to dryness. A white, solid residue remained. This residue was dissolved with 4 drops each of the nitric acid and the hydrofluoric acid. The dissolved sample was diluted with 10 ml of deionized water. This sample constituted a "silicon crystal blank." An "acid blank" was prepared in the same manner, with the exclusion of the silicon.

The GFAA spectroscope utilized was a Spex-40, manufactured by Varian Associates, Inc. The instrument was operated using the instructions of the manufacturer. The graphite tubes of the analyzer were fired several times until no spurious background peak was observed.

About 20–40 microliters of the liquid sample were injected into the GFAA spectroscope. The GFAA spectroscope had an automated injection, analysis, and readout out system that gave results of individual metal content of the solution in units of nonogram/milliliter (ng/ml).

Five individual silicon crystal blank solutions and five individual acid blank solutions were prepared. A sample of each blank solution, and in most cases replicate samples, were injected into the GFAA spectroscope. Table 1 is a summary of the GFAA results for iron and nickel content. In table 1, the results for iron and nickel in ng/ml are designated as "Fe" and "Ni", respectively for the silicon crystal blank samples, denoted as "Si Blank", and the acid blank, denoted as "Acid Blank". The results reported are the average of the samples analyzed and the standard deviation of these results, denoted as "Ave." and "Std. Dev.", respectively.

TABLE 1

| | Si Blank | | Acid Blank | |
| --- | --- | --- | --- | --- |
| | Fe | Ni | Fe | Ni |
| Ave. | 3.006 | 0.297 | 3.474 | 0.341 |
| Std. Dev. | 0.926 | 0.549 | 0.942 | 0.270 |

From these analytical results, the detection limits at a 95% statistical confidence level (D.L.) of this procedure are calculated using the following relationship:

D.L. = 2(Std. Dev. Si Blank + Std Dev. Acid Blank)
× Vol. of Sample Solution/Wt. of Crystal Sample Therefore, for iron, $$D.L. = 2(0.926 \text{ ng/ml} + 0.942 \text{ ng/ml}) \times 10 \text{ ml}/0.1 \text{ g}$$
$$= 374 \text{ part per billion by weight (ppbw)}$$
$$= 187 \text{ part per billion, atomic (ppba)}.$$

Further, for nickel, $$D.L. = 2(0.549 + 0.270) \times 10/0.1$$
$$= 164 \text{ ppbw}$$
$$= 82 \text{ ppba}$$

Table 2 is a summary of the results of the detection limits for several metals using the above method and calculations.

TABLE 2

| Metal | D.L., ppba |
| --- | --- |
| Aluminum | 240 |
| Chromium | 16 |
| Copper | 40 |
| Iron | 180 |
| Manganese | 8 |
| Molybdenum | 240 |
| Nickel | 80 |
| Titanium | 1200 |

The above results demonstrate that the detection limits for many metals in silicon is significantly higher than the instrument sensitivity due to factors such as contamination problems in handling.

EXAMPLE 2:

Samples of polycrystalline silicon were treated by the float-zone refining method to concentrate the trace metals in a melt zone and a corresponding solid zone. The solid zone concentrated in trace metals was analyzed by GFAA.

Individual rods of polycrystalline silicon were first cored with a 19 mm diameter stainless steel core drill with diamond mounted on the end. The cores taken were typically 3–4 inches long and weighed approximately 40 g.

The individual cores were degreased with trichloroethylene and etched with acid, in a manner similar to preparation of samples discussed below. The etched cores were dried in a Class 100 clean air hood for about 1 hour.

The float-zone refining method is a known technique. The procedure utilized is similar to that described by Dietz et al., Cryst.: Growth, Prop.,Appl., 5(1981), pp. 1–42 . For this study, the float-zone refiner was a Siemens VZA-3, manufactured by Siemens Energy and Automation, Inc.

The metals-containing polycrystalline rods of silicon were converted to single crystals essentially free of metals in the float-zone refiner. The heater of the refiner traversed the length of the rod at a rate of about 2mm/min. The melt zone which contained essentially all the metals was allowed to cool in such a manner that a tip formed on the side of the frozen melt zone. Cooling was effected by reducing power to the heater over a period of about 5 seconds so that tip formation was visually noted. The heater coil was removed from around the single crystal rod, and the rod was cooled to ambient temperature.

The tip formed on the side of the frozen melt zone was removed by scribing with a diamond stylus. The frozen melt zone was removed by sawing it away from the crystal rod with a diamond-tipped saw. The frozen melt zone weighed about 1.0 to 1.5 g. The frozen tip weighed about 0.06 g.

The silicon samples, frozen melt zone and frozen tip, were prepared as follows. For the frozen melt zone, a silicon sample of approximately 1 g was contacted with trichloroethylene for about 1 minute to remove surface grease. The sample was rinsed, successively, with acetone and methanol. The trichloroethylene and acetone were electronic grade materials. The methanol was micro-process grade.

The sample was then etched three times with a 5:1 (volume/ volume) mixture of concentrated nitric acid and hydrofluoric acid. The concentrated nitric acid was electronic grade material. The concentrated hydrofluoric acid was electronic grade material.

The etched silicon sample was then placed into about 20 ml of a , 2:1 (volume/volume) mixture of ultra pure concentrated nitric acid and hydrofluoric acid. The ultra pure nitric acid and hydrofluoric acid were doubly distilled material. The silicon was allowed to be dissolved in the acid mixture. Silicon was liberated as vapors of silicon fluorides. The remaining acid solution was dried overnight in a Telfon ® container on a hot plate at low heat with an argon purge. A trace amount of white solid residue from oxidation of silicon with nitric acid resulted. The solid residue was dissolved with about 0.5 ml each of the ultra pure acids. The sample was then diluted to 10 ml with distilled water.

The frozen tip was prepared in a similar fashion without etching and with reduced proportions of acids.

The aqueous samples so prepared were then analyzed by the GFAA technique utilized in Example 1. A blank utilizing a silicon sample, essentially free of metals, was run with each sample.

Four polycrystalline silicon samples were evaluated. These samples are designated as Sample A, B, C, and D, respectively.

Table 3 is a summary of the GFAA iron analyses of frozen melt zone and frozen tip of the the single crystal prepared from the polycrystalline silicon samples. In Table 3 results of analysis for iron are reported in ng. This result was obtained taking the output from the GFAA which is reported in ng/ml and multiplying by the size of the original sample solution which is about 10 ml. The iron analyses for the frozen melt zone, less the tip, and the tip itself are designated as "F.M.Z." and "Tip", respectively; the ratio of the metals content of the tip to the total frozen melt zone, expressed as a fraction of the total, is designated "Tip/Total".

TABLE 3

| Sample | F.M.Z | Tip | Total | Tip/Total |
| --- | --- | --- | --- | --- |
| A | 200 | 134 | 334 | 0.40 |
| B | 740 | 430 | 1170 | 0.37 |
| C | 2500 | 930 | 3430 | 0.27 |
| D | 20300 | 11300 | 33600 | 0.36 |

These above results were utilized to calculate the iron content, in ppba, of the starting polycrystalline silicon samples. Table 4 is a summary of these results.

TABLE 4

| Sample | Iron Content, ppba |
|---|---|
| A | 8 |
| B | 29 |
| C | 84 |
| D | 840 |

The above results demonstrate that about 25 to 40 percent of a trace metal concentrated by the float-zone refining technique can be contained in the tip of the frozen melt zone. Additionally, these results demonstrate the use of the float-zone refining technique coupled with GFAA for the analyses of trace metals.

EXAMPLE 3:

A silicon sample was prepared by doping the sample with iron, nickel, copper, and chromium and pulling a single crystal by the Czochralski (CZ) crystal pulling method. This crystal pulling method is known in the art and is similar to the procedure described in Kirk-Othmer, *Encyclopedia of Chemical Technology*, 2nd Ed., Vol. 17, pp. 862–865. The crystal pulling apparatus was a CG-800 purchased from Hamco, Inc.

The proper amount (mg to g) of trace metals were added to 2.5 kg. of silicon, essentially free of metals, in a quartz crucible. The crucible charge was melted electrically. The crucible charge consisted of:

| 2.5 kg | Silicon |
|---|---|
| 0.0784 g | Copper |
| 3.9178 g | Iron |
| 0.2056 g | Nickel |
| 1.6910 g | Chromium |

The copper, iron, nickel, and chromium were added in the form of free metal powders.

A high-purity single crystalline silicon seed was introduced and a silicon rod approximately 19 mm in diameter and 50 inches in length was pulled at a 5–6 inch/hr pull rate.

The rod was cut with a diamond-tipped saw into alternate 4-inch and 1-inch sections. Several adjacent pairs of sections were chosen for parallel analyses. The 4-inch sections were subjected to float-zone refining as in Example 2. The 1-inch sections were analyzed by neutron activated analyses (NAA) at the Research Reactor Facility, at the University of Mo., Research Park, Columbia, Mo. These pairs of samples are designated as Samples E, F, G, H, J, and K, respectively.

For the samples subjected to float-zone refining, determination of metals content of the bulk sample were based upon the analysis of the tip of the frozen melt zone. The tip was separated from the frozen melt zone and prepared for GFAA as described in Examples 1 and 2. From the results of GFAA, the trace metals concentration of the bulk silicon sample was calculated, assuming that one-third of the trace metals were included in the tip of the frozen zone.

The trace metals concentration of the samples is calculated from from GFAA results using the following relationship:

$$C_t = 3 \times [C_{tip} - C_b] \times V_{tip}/W_t,$$

wherein, $C_t$ = the concentration of the metal in the total silicon sample, ng/g $C_{tip}$ = GFAA analysis of sample solution prepared from the frozen tip, ng/ml $C_b$ = GFAA analysis of blank solution, ng/ml $V_{tip}$ = volume of the sample solution, ml $W_t$ = weight of the total silicon sample, g The calculated results are converted from ppbw to ppba.

Table 5 is a summary of the trace metals concentrations of these pairs of samples as determined by GFAA and NAA analyses. The results reported in Table 5 are the concentration of trace metals, expressed in ppba; results from neutron activation analysis are designated "NAA"; results from GFAA are designated "GFAA"; the metals reported are nickel, iron, copper, and chromium, designated as "Ni", "Fe","Cu", and "Cr", respectively.

TABLE 5

| Sample | Ni GFAA | Ni NAA | Fe GFAA | Fe NAA | Cu GFAA | Cu NAA | Cr GFAA | Cr NAA |
|---|---|---|---|---|---|---|---|---|
| E | 3.9 | 6.8 | 8.0 | 5.0 | 2.7 | 4.9 | 0.8 | 1.3 |
| F | 3.2 | 6.9 | 6.9 | 5.4 | 2.2 | 5.5 | 0.9 | 1.5 |
| G | 3.7 | 6.3 | 11.0 | 5.2 | 2.4 | 5.3 | 0.8 | 1.4 |
| H | 5.0 | 6.8 | na | 5.8 | 5.6 | 5.7 | 1.1 | 1.5 |
| J | 4.8 | 7.1 | 6.2 | 5.9 | 3.3 | 5.0 | 1.0 | 1.6 |
| K | 6.3 | 6.9 | 6.8 | 5.9 | 4.3 | 5.5 | 1.4 | 1.9 |

The above results demonstrate a method in which the tip of the frozen molten zone can be utilized for GFAA analysis to generate a reliable measure of the trace metals content of high-purity silicon.

EXAMPLE 4:

Four cores, each, of several rods of polycrystalline silicon were taken. These cores was analyzed by the float-zone refining/GFAA procedure described above and the NAA method. The polycrystalline rods are designated as Samples L, M, N, P, and Q, respectively.

Table 6 is a summary of the calculated results of iron content from GFAA and the reported results of NAA, both reported in ppba. The results of analyses of each core and the average of these two results is reported

TABLE 6

| | GFAA | | | NAA | | |
|---|---|---|---|---|---|---|
| Sample | Core 1 | Core 2 | Ave. | Core 3 | Core 4 | Ave. |
| L | 20 | 21 | 21 | 50 | 10 | 30 |
| M | 15 | 6 | 11 | 6 | 7 | 7 |
| N | 13 | 32 | 23 | 14 | 14 | 14 |
| P | 9 | 7 | 8 | 14 | 2 | 8 |

TABLE 6-continued

| | GFAA | | | NAA | | |
|---|---|---|---|---|---|---|
| Sample | Core 1 | Core 2 | Ave. | Core 3 | Core 4 | Ave. |
| Q | 21 | 8 | 15 | 20 | 5 | 13 |

The above results further demonstrate the capabilities of the instant invention to analyze to trace levels of metals in a

What is claimed is:

1. A method for analyzing for and quantifying trace metals content of a semiconductor material, the method comprising
    (G) performing float-zone refining of a sample of the semiconductor material by passing a heating element along the sample, thereby creating a melt zone containing essentially all the trace metals content of the semiconductor material;
    (H) controlling cooling of the melt zone so that the melt zone forms a solid zone with a frozen tip being formed, the frozen tip containing a significant portion of the trace metals content of the sample of the semiconductor material;
    (I) separating the frozen tip from the solid zone;
    (J) preparing the frozen tip for trace metals analysis;
    (K) analyzing the frozen tip with a means for trace metals analysis; and
    (L) calculating total trace metals content of the sample of the semiconductor material from analysis of the frozen tip.

2. A method according to claim 1, wherein preparing the frozen tip for metals analysis comprises converting the frozen tip into an aqueous solution suitable for trace metals analysis.

3. A method according to claim 2, wherein the means for trace metals analysis is selected from a group consisting of atomic absorption spectroscopy, emission spectroscopy, ion chromatography, and mass spectroscopy.

4. A method according to claim 3, wherein the means for trace metals analysis is graphite furnace atomic absorption spectroscopy.

5. A method according to claim 1, wherein preparing the frozen tip for metals analysis comprises treating the frozen tip to remove surface contaminants.

6. A method according to claim 5, wherein the means for trace metals analysis is selected from a group consisting of atomic absorption spectroscopy, electron spectroscopy, emission spectroscopy, transient spectroscopy, X-ray spectroscopy.

7. A method according to claim 1, wherein the trace metals are selected from a group consisting of aluminum, chromium, copper, iron, manganese, molybdenum, nickel, and titanium.

8. A method according to claim 1, wherein the solid zone is in a range from about 0.1 to 10 weight percent of the sample of the semiconductor material; and the frozen tip is in a range from about 1 to 5 weight percent of the solid zone.

9. A method according to claim 1, wherein the semiconductor material is silicon.

10. A method according to claim 2, wherein the controlled cooling of the melt zone to form the solid zone with the frozen tip is effected by
    (M) reducing electrical power to the heating element over a period of about 5 to 10 seconds;
    (N) removing the heating element from around the sample of the semiconductor material so that the frozen tip does not touch the heating element;
    (O) cooling the semiconductor material, containing the solid zone with the frozen tip, to ambient temperature.

* * * * *